Figure 1:
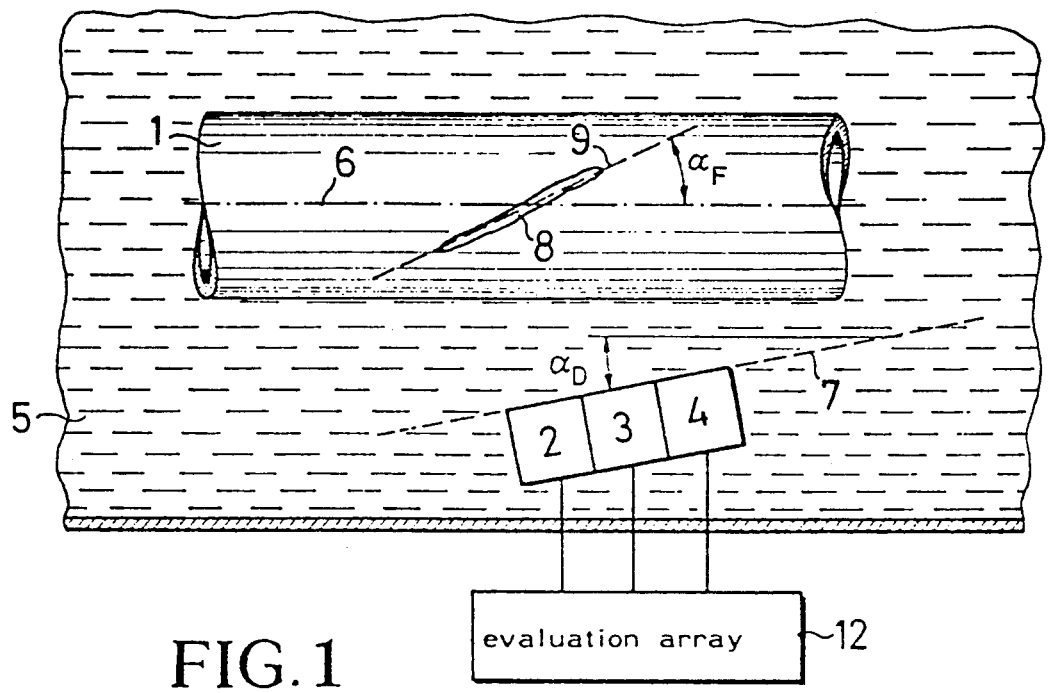

United States Patent [19]

Sternberg et al.

[11] Patent Number: 5,165,280
[45] Date of Patent: Nov. 24, 1992

[54] DEVICE FOR TESTING OF OBLONG OBJECTS BY MEANS OF ULTRASONIC WAVES

[75] Inventors: Walter Sternberg, Alzenau; Michael Schmeisser, Hanau; Michael Strauss, Alzenau-Kälberau, all of Fed. Rep. of Germany

[73] Assignee: Nukem GmbH, Fed. Rep. of Germany

[21] Appl. No.: 605,360

[22] Filed: Oct. 30, 1990

[30] Foreign Application Priority Data

Aug. 28, 1990 [DE] Fed. Rep. of Germany ....... 4027161

[51] Int. Cl.⁵ .............................................. G01N 29/10
[52] U.S. Cl. ........................................ 73/622; 73/625; 73/641
[58] Field of Search ................ 73/622, 624, 625, 627, 73/628, 641, 626

[56] References Cited

U.S. PATENT DOCUMENTS

| 3,228,232 | 1/1966 | Proctor | 73/628 |
| 3,683,680 | 8/1972 | Johnson et al. | 73/628 |
| 4,275,598 | 6/1981 | Engl | 73/622 |
| 4,523,468 | 6/1985 | Derkacs et al. | 73/628 |

FOREIGN PATENT DOCUMENTS

| 0063447 | 4/1982 | Japan | 73/625 |
| 1293638 | 2/1987 | U.S.S.R. | 73/627 |
| 1416904 | 8/1988 | U.S.S.R. | 73/626 |

*Primary Examiner*—Hezron E. Williams
*Assistant Examiner*—Rose M. Finley
*Attorney, Agent, or Firm*—Cushman, Darby & Cushman

[57] ABSTRACT

The object of the invention is a device for ultrasonic inspection of cylindrical objects. A transmitting ultrasonic transducer generates ultrasonic waves that are acoustically irradiated into the respective object via a coupling medium. At least three ultrasonic transducers are arranged in a row next to one another along a line. The outer ultrasonic transducers are receiving ultrasonic transducers. The other ultrasonic tranducers are transmitting or transmitting/receiving ultrasonic transducers. The line is inclined against the longitudinal axis of the object by an angle which is between 0° and 45°.

10 Claims, 2 Drawing Sheets

DEVICE FOR TESTING OF OBLONG OBJECTS BY MEANS OF ULTRASONIC WAVES

DESCRIPTION

The present invention relates to a device for ultrasonic inspection of cylindrical objects provided with at least one ultrasonic transducer constituting a transmitter for ultrasonic waves which are transmitted via a coupling medium into an respectively object, and with receiving means for ultrasonic waves reflected by faults in the object and causing in the receiving means output signals which are evaluated in evaluation means for detecting faults in the object.

In known devices for ultrasonic inspection excitation pulses are generated by inspection circuits and activate ultrasonic oscillators, for example in the form of ultrasonic transducers heads, for emission of ultrasonic waves. The ultrasonic transducers are coupled to the test specimens via a medium, for example water. For the reception of ultrasonic waves reflected in the test specimen, ultrasonic transducers are provided that convert ultrasonic waves into electrical signals which are selected, amplified and evaluated by inspection circuits with for example time gates and orifices. The evaluation relates to the amplitudes of the signals and to the delays between the signals. The test information, e.g. the amplitudes, limit value overshoots, delays etc. can be acquired, evaluated an recorded with a data processing facility and displayed on a monitor.

For example when skew-rolling products in a rolling mill, faults can occur in these products that are at an angle of inclination in relation to the longitudinal axis. Faults may also be present in the material prior to skew-rolling. If faults of this type show a slanting angle of approx. 45° to the longitudinal axis of the respective object, only the angular position changes, but not the orientation of the fault during rolling. Faults of this type are usually in the range between 5° and 50° after rolling.

Faults of this type inclined against the longitudinal axis must also be detected lug the non-destructive inspection. A possible device for detection of the faults described above comprises annularly arranged ultrasonic transducers operating as transmitter and/or receivers for ultrasonic waves. As a general principle, only those faults are measured that run below an angle of 45° or 135° respectively to the longitudinal axis of the workpiece. The ultrasonic testing heads must be aligned individually as regards their acoustic irradiation angle so that those faults running at an angle to the longitudinal axis are also detected. A device of this type is expensive. The setting of the ultrasonic testing head is time-consuming and in addition only a relatively low testing speed is feasible.

An object of the present invention is to provide a device for detecting faults having slanting angle of substantially less than 90° to the longitudinal axis of the object as simply as possible.

According to the invention at least three ultrasonic transducers arranged in a row are arranged along a line next to one another or in steps with sound-transmitting or sound-receiving surfaces parallel to one another and to the line. The outer ultrasonic transducers of the row constitute receivers for ultrasonic waves only. The transducer or transducers surrounded by the outer transducers constitute either transmitters only or transmitters and receivers for ultrasonic waves. The line is inclined against the longitudinal axis of the object by a slanting angle in the range between 5° and 20°.

A relative movement takes place between the object and the row of ultrasonic transducers during the test. The surface sections of the object are moved one after the other past the ultrasonic transducers in a helical manner. The ultrasonic transducers can be stationary while the object is being conveyed in its longitudinal direction and turned at the same time. The reverse arrangement is also possible.

While longitudinal and transverse faults can be detected in the usual way, the device described in the above allows "inclined faults" too to be found with simple means. In particular, three ultrasonic transducers are arranged in a row, which makes for a particularly simple design. The angle between the longitudinal axis of the object in question and the direction of the effect of a tool, such as skewed rollers, is set for treatment of the object and is therefore usually predetermined. Based on this angle, it is possibly to approximately predict the change in the angular position of inclined faults during a rolling operation, for example. The device described above permits particularly good fault when the inclination of the line of ultrasonic transducers is one third of the slanting angle of a fault to the longitudinal axis of the object in test.

To detect faults with, for example, an angle of inclination of 15° against the longitudinal axis of an object the slanting, a angle of the line must be provided of 5° to the longitudinal axis of the respective object. With slanting angles of the lines of 10°, 15° or 18° to the longitudinal axis, it is possible in principle to detect faults with up to 30°, 45° or 60° inclination respectively against the longitudinal axis.

The centre ultrasonic transducer for transmitting ultrasonic waves can also be constituted as a receiving ultrasonic transducer.

In a preferred embodiment, amplifiers are connected to the ultrasonic transducers in an evaluation device. The amplification factors of the amplifiers for the receiving ultrasonic transducers arranged on either side of a transmitting ultrasonic transducer are set higher than the amplification factor for the transmitting/receiving ultrasonic transducer. In particular, the amplification factor is set up to 10 times higher than the amplification factor of the amplifier connected to the transmitting-/receiving ultrasonic transducer.

It has become apparent that the receiver of the transmitting/receiving ultrasonic transducer in an array as described above generates, in the case of inclined faults with an inclination of the fault against the longitudinal axis of three times the inclination of the line of ultrasonic testing heads, higher amplitudes of the fault signals than the adjacent ultrasonic transducers provided the faults do not diverge by more than 5° from the "ideal inclination". If the actual faults do diverge by more than 5° from the ideal inclination at which the inclination of the line of ultrasonic transducers is ⅓ of the inclination of the assumed faults, the receiving ultrasonic testing heads arranged on either side of the transmitting ultrasonic transducer generate higher amplitudes. Amplitudes of this type are completely sufficient for fault detection, so that the use of the transmitting ultrasonic transducers as a receiver also can be dispensed with in order to reduce the measurement technology expenditure.

The transducer line can comprise single testing transducers arranged in a row and in steps to achieve the same distance to the object for each transducer. The result is identical acoustic irradiation characteristics that ensure even pickup of the signals. Naturally the normal lines extending from the testing head surfaces (sound-reflecting surfaces) run parallel to one another and perpendicular to the line described above.

The stepped arrangement ensures furthermore a shallow construction depth. This is an advantage for the volume of the test basin and the design of the mechanical system.

Preferably, more than three transducers can be arranged along a line to achieve a higher test speed. Preferably groups of three subsequent transducers are connected to form a measuring unit comprising a receiving, a transmitting and a further receiving head. The transmitting ultrasonic transducer is also provided to operate as a receiving ultrasonic transducer.

A further proposal worthy of note provides for divergence of the acoustic irradiation angles of the individual transducers, i.e. individual settability. As a result, faults can be detected in an even greater angular range.

Furthermore, it must be noted as a general point that in the theory in accordance with the invention, not only inclined faults formed by treatment of the workpiece can be detected, but also those faults that can be present in the test speciment anyway, for example cavities in the raw material.

Further details, advantages and features of the invention are made clear not only in the claims and features to be taken therefrom, alone and/or in combination, but also in the following description of preferred embodiments to be found in the drawing.

The drawings show in

Figure 2:
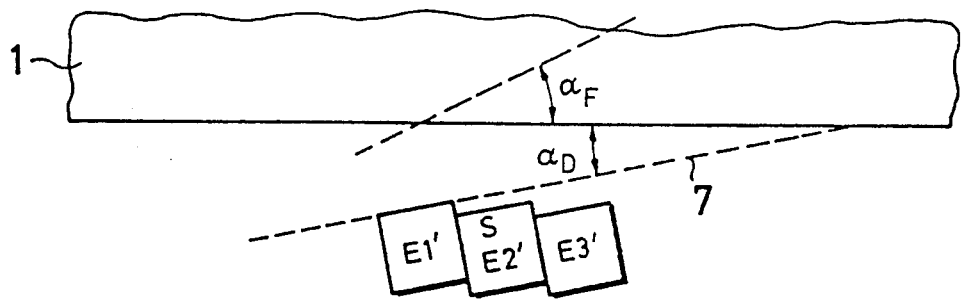
Figure 3:
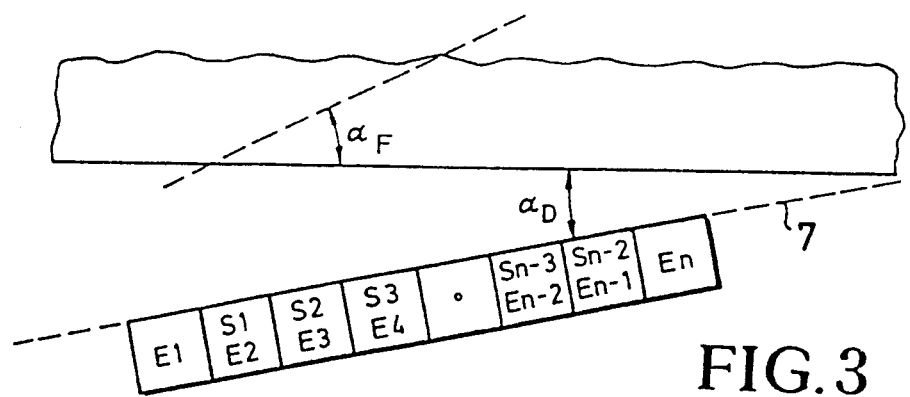
Figure 4:
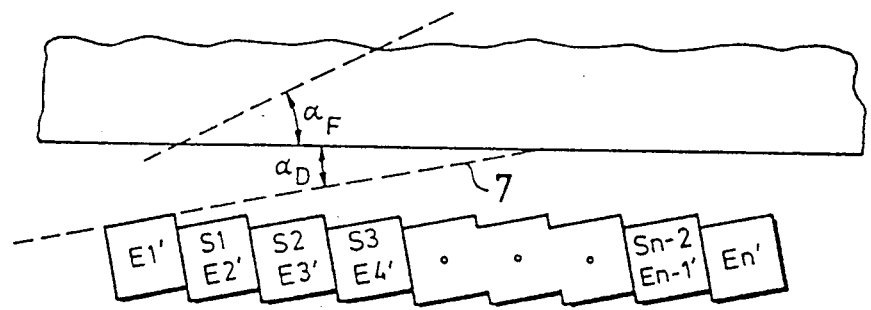
Figure 5:
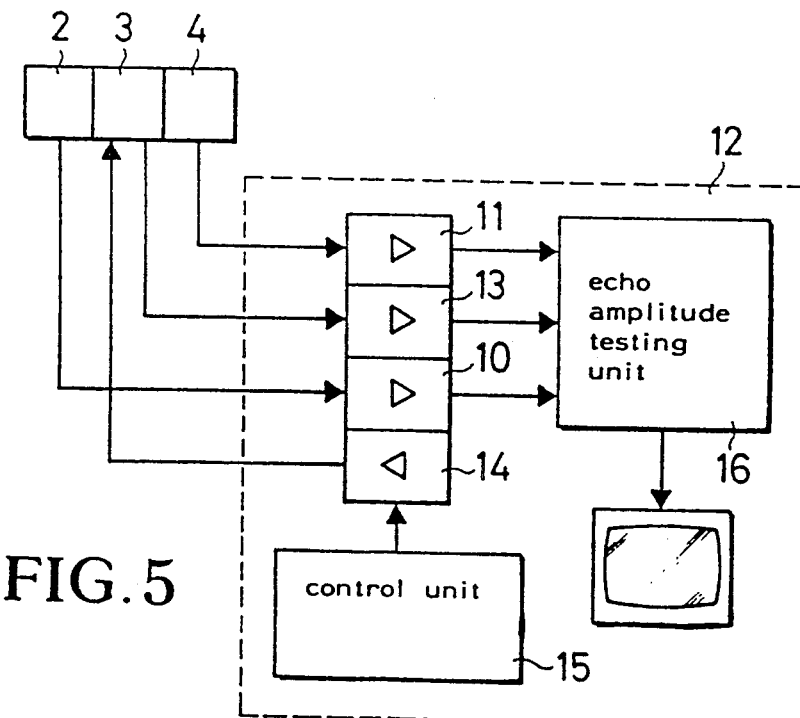

FIG. 1 a principle drawing of a first embodiment of a device in accordance with the invention for ultrasonic inspection of cylindrical objects using a measuring array comprising three transducers, FIG. 2 a principle drawing of a second embodiment of a device in accordance with the invention for ultrasonic inspection of cylindrical objects using a measuring array probe comprising three transducers, FIG. 3 a principle drawing of a measuring array probe comprising more than three transducers and corresponding to the first embodiment of the device in accordance with the invention for ultrasonic inspection of cylindrical objects, FIG. 4 a principle drawing of a measuring array probe comprising more than three transducers and corresponding to the second embodiment of the device in accordance with the invention for ultrasonic inspection of cylindrical objects and FIG. 5 details of the devices shown in FIGS. 1-4.

A device for ultrasonic inspection of cylindrical objects with regular geometric surface, in particular pipes (1) or bars, contains three ultrasonic transducers (2), (3), (4) arranged in a row next to one another.

The ultrasonic transducers (2), (3) and (4) can comprise an oscillator acting as three single oscillators following division of an electrode.

The centre ultrasonic transducer (3) operates as a transmitting ultrasonic transducer or as a transmitting-/receiving ultrasonic transducer. The two external ultrasonic transducers (2), (4) are receiving ultrasonic transducers.

Due to the fact that the ultrasonic transducers (2), (3) and (4) practically have a "base oscillator", the distance from the pipe (1) varies from transducer to transducer.

The pipes (1), of which only one is shown in FIG. 1, are moved in a water bath (5) in the direction of their longitudinal axis (6) past the ultrasonic transducers (2), (3), (4) and turned simultaneously such that the various surface sections pass the ultrasonic transducers (2), (3), (4) in a helical form one after the other.

It is also possible to arrange more than three ultrasonic transducers in a row next to one another (FIG. 3 or FIG. 4). With more than three ultrasonic transducers, three consecutive transducers (E1), (E2) and (E3), or (E2), (E3) and (E4) . . . are connected as one measuring unit in each case, the two outer ultrasonic transducers being receiving ones while the intermediate one is at least a transmitting and if necessary also a receiving ultrasonic transducer.

The possibility exists to move the ultrasonic transducers (2) to (4) or (E1) to (En) past the pipe (1) in helical manner.

The ultrasonic transducers (2), (3), (4) (FIG. 1) and if necessary more ultrasonic transducers (E1) to (En) (FIG. 3) are arranged in a row along a line (7). In FIGS. 2 and 4 the measuring units comprise individual transducers (E1') . . . (En') in a row, the sound-receiving oscillator surfaces running parallel to one another and parallel to the line (7).

The construction of line with individual transducers has the advantage that a substantially constant distance between the respective transducer (E1') . . . (En') and the pipe (1) is achieved, and thereby constant acoustic irradiation characteristics.

In FIG. 4—as in FIG. 3—there are shown three consecutive transducers (E1') to (E3') . . . (En-2') to (En') which are connected to form one measuring unit, with the outer transducers operating as receivers one and the enclosed transducer in each case being at least a transmitting ultrasonic transducer.

The ultrasonic transducers can be plane or line-focussed.

Faults can be present in the pipes (1). As an example, FIG. 1 shows a fault (8) extending substantially along the line (9) that is inclined below an angle $\alpha_F$ against the longitudinal axis (6), that is greater than 0° and less than 90° (naturally a fault can also be between 90° and 180°, which is not mentioned for simplicity's sake).

The pipes (1) are treated in many cases by skew rollers, for example. The skew rolling operation alters the angular positions of the faults, i.e. the angles $\alpha_F$ of the line (9) passing through the fault in its longitude or width against the longitudinal axis (6) are reduced by skew rolling, so that hardly any angles $\alpha_F$ occur in the range between 70° and 90° once skew rolling is completed. If faults are present at the start of the skew rolling operation that are substantially below an angle of 45° to the longitudinal axis (6), then their position changes, with the slanting possibly being in the range between 5° and 40° after rolling. The direction of the faults, i.e. their orientation, is not however changed.

To pick up faults of this type, referred to as "inclined faults", the ultrasonic transducers (2), (3), (4) are used, arranged adjacently on a support, for example, and linked to the pipe (1) by the water. The three or more ultrasonic transducers form the transducerline and can be adjusted together.

To reliably detect faults with angles of inclination $\alpha_F$ other than 0° and 90° (or 90° and 180° respectively), the ultrasonic transducers (2), (3) and (4) are inclined against the longitudinal axis (6) with their line (7) below an angle $\alpha_D$ differing from 0° and 90° (or 90° and 180° respectively). It has become clear that the angle of inclination of the line (7), i.e. the slanting angle $\alpha_D$ of the transducer line against the longitudinal axis (6), should be one third of the inclination angle $\alpha_F$ of a fault against the longitudinal axis (6) in order to detect this fault with a high echo signal. The acoustic irradiation angle is then normal to the line (7) of the testing head line. With inclination angles of 5°, 10°, 15° or 18° of the line (7) or of the transducer line against the longitudinal axis (6), faults with angles of inclination of approx. 15°, 30°, 45° and 60° are adequately covered.

The transducer line itself can be offset in relation to the plane passing horizontally through the centre axis (6) of the pipe (1) such that an acoustic irradiation angle of preferably 19° is obtained (acoustic irradiation angle equal to angle between impingeing ultrasound and sounder at impingement point).

The receiving ultrasonic transducers (2) and (4) are each provided with amplifiers (10), (11) located in an evaluation array (12). The transmitting/receiving ultrasonic transducer (13) is connected by its receiver part to an amplifier (14). The amplifier (14) is subjected to control signals from a transmitting and receiving cycle control (15). The amplification factors of the three amplifiers (10), (11), (13) are adjustable to various values. The outputs of amplifiers (10), (11), (13) are connected to a unit (16) for echo amplitude testing, this device being a data processing system, for example a computer also having a monitor (17). The transmitting and receiving cycle control, the device (16) and the monitor (17) are integral parts of the evaluation array (2) generating a visual and/or audible signal in the event of a fault and/or recording the fault on a storage medium not shown in detail.

The amplifiers (10), (11) of the receiving ultrasonic transducers on either side of the transmitting ultrasonic transducer have an amplification factor up to 10 times that of amplifier (13). This applies as a general principle for all receiving ultrasonic transducers on either side of a transmitting ultrasonic transducer. It has been shown that in the case of faults with an inclination in the angle range between approx. ±5° and ±15° based on $\alpha_F$, the received ultrasonic echo preferably goes to the receiving ultrasonic transducers (2), (4), i.e. to the ultrasonic transducers on either side of a transmitting ultrasonic transducer. To reduce the expenditure on the receiver side, therefore, the receiving function of the ultrasonic transducer (3) can be dispensed with. This also saves the need for the entire corresponding receiving channel. The receiving part of the ultrasonic transducer (3) provides after receiving ultrasonic signals a higher amplitude than the receibing ultrasonic transducers only for inclined faults with an inclination $\alpha_F$ approximately of 3 $\alpha_D$.

The discrimination of faults within windows of time set inside the evaluation array (12) takes place when the threshold value is exceeded, i.e. normally. Windows of time can also be shut off when no discrimination of the received ultrasonic echo signals is required. The window width is settable. The start of window can be derived from a triggering cycle of the transmitting and receiving cycle control (15).

Faults are determined by assessing the ultrasonic echo amplitude received inside the set window of time at every test cycle generated by the transmitting and receiving cycle control (15). A separate threshold value can be preset for every window and also for every receiving channel.

We claim:

1. A device for ultrasonic inspection of cylindrical objects comprising at least one ultrasonic transducer comprising means for transmitting ultrasonic waves and receiving ultrasonic waves reflected by flaws in said cylindrical object to generate output signals, a coupling medium, means for mounting a cylindrical object to receive said ultrasonic waves via said coupling medium, and means for evaluating said output signals and thereby detecting faults in said cylindrical object, said ultrasonic transducer comprising at least three transducer elements arranged in a row next to one another along a receiving line or in steps along a line with their sound transmitting or sound receiving surfaces parallel to one another and to a receiving line, the outer transducer elements being receiving-only transducer elements and a transducer element or transducer elements surrounded by said receiving-only transducer element being transmitters or transmitter-receivers, said receiving line being inclined from the longitudinal axis of said object by an angle in the range between 5° and 20°.

2. A device as set forth in claim 1 in which said angle is about one-third of the angle between said faults and the longitudinal axis of said object.

3. A device as set forth in claim 1 in which a transducer element surrounded by said receiving-only transducer elements is a transmitter-only transducer if the angle between said faults and said longitudinal axis is smaller than three times the angle between said receiving line and said longitudinal axis minus 5° or if the angle between said faults and said longitudinal axis is larger than three times the angle between said receiving line and said longitudinal axis plus 5°.

4. A device as set forth in claim 1 in which said evaluating means comprise amplifiers connected to said transducer elements, said amplifiers having adjustable amplification factors.

5. A device according to claim 4 in which said evaluating means includes amplifiers connected to said outer transducer elements and amplifiers connected to said transmitter-only or transmitter-receiver transducer elements, and the amplifiers connected to said outer transducer elements have amplification factors in the range up to ten times the amplification factors of amplifiers connected to said transmitter-only or transmitter-receiver transducer elements.

6. A device as set forth in claim 1 in which said evaluating means includes means for inspecting the received ultrasonic signals for fault-criterion.

7. A device as set forth in claim 1 having more than three ultrasonic transducer elements, with groups of three consecutive transducer elements constituting measuring units, and including means to operate said measuring units consecutively.

8. A device as set forth in claim 7 in which an ultrasonic transducer element is used as a transmitting transducer of one unit and a receiving transducer of a previous unit.

9. A device as set forth in claim 1 in which the distances between successive transducer elements are equal.

10. A device as set forth in claim 1 including plural transducers in which the acoustic irradiation angles of the transducers differ from one another.

* * * * *